(12) United States Patent
Greco

(10) Patent No.: US 8,802,162 B2
(45) Date of Patent: Aug. 12, 2014

(54) L-CITRULLINE FOR TREATING ENDOTHELIAL DYSFUNCTION AND ERECTILE DYSFUNCTION

(75) Inventor: Ermanno Greco, Rome (IT)

(73) Assignee: Androsystems S.R.L. (IT)

( * ) Notice: Subject to any disclaimer, the term of this patent is extended or adjusted under 35 U.S.C. 154(b) by 0 days.

(21) Appl. No.: 12/935,782

(22) PCT Filed: Mar. 10, 2009

(86) PCT No.: PCT/EP2009/052799
§ 371 (c)(1), (2), (4) Date: Sep. 30, 2010

(87) PCT Pub. No.: WO2009/121687
PCT Pub. Date: Oct. 8, 2009

(65) Prior Publication Data
US 2011/0044965 A1  Feb. 24, 2011

(30) Foreign Application Priority Data
Apr. 2, 2008  (IT) ............................. MI2008A0567

(51) Int. Cl.
*A61K 36/00* (2006.01)
*A61K 36/28* (2006.01)
*A61K 38/43* (2006.01)
*A61K 31/195* (2006.01)

(52) U.S. Cl.
USPC ........... 424/725; 424/94.1; 424/765; 514/564

(58) Field of Classification Search
None
See application file for complete search history.

(56) References Cited

U.S. PATENT DOCUMENTS

2005/0256192 A1  11/2005  Gardiner et al.

FOREIGN PATENT DOCUMENTS

| DE | 43 41 000 A1 | | 6/1995 |
|---|---|---|---|
| WO | WO 2006/002096 | * | 1/2006 |
| WO | WO 2006/002096 A | | 1/2006 |
| WO | WO 2006/113389 A | | 10/2006 |
| WO | WO 2007/114903 A | | 10/2007 |

OTHER PUBLICATIONS

Drewes, et al. (2003) Phytochemistry 62 pp. 1019-1025.*
Fernandez et al. (1998) Journal of Ethnopharmacology 62; pp. 25-34.*
Jeremy et al. (2007) Inter. J. Impotence Res. 19; pp. 265-280.*
Mass et al. (2002) Vascular Medicine 7: pp. 213-225.*
Tenorio et al. (2005) Fitoterapia 76: pp. 204-209.*
Shukla et al. (2008) BJUI 103, 98-103.*
Drewes S E et al:"Recent findings on natural products with erectile-dysfunction activity"Phytochemistry,Pergamon Press,GB, vol. 62,No. 7,Apr. 1, 2003,pp. 1019 . . .
Durackova Z et al:Lipid metabolism and erectile function improvement by Pycnogenol,extract from the *Pinus pinaster* in patients suffer from erectile dysfunction—a pilot . . . 2003.
Sommer F et al:"Evaluation of tetrahydrobiopterin(BH4)as potential therapeutic agent to treat erectile dysfunction"Asian Journal of Andrology,Science Press,Shanghai,CN,vol. 8, 2006.
Dumitrescu Cristian et al:"Tetrahydrobiopterin and NADPH treatment reverses endothelial dysfunction in post-ischemic hearts"Circulation;77th Scientific Meeting of the . . . 2009.
Tenorio F A et al:"Vasodilator activity of the aqueous extract of *Viscum album*"Fitoterapia,IDB Holding,Milan,IT,vol. 76,No. 2,Mar. 1, 2005,pagg.204-209,XP025264959.
Toda N et al:"Nitric oxide and penile erectile function"Pharmacology and Therapeutics,Elsevier,GB,vol. 106,No. 2,May 1, 2005,pagg,233-266,XP004870345 ISSN:0163-7258.
Sullivan M E et al:"Nitric oxide and penile erection:is erectile dysfunction another manifestation of vascular disease?"Cardiovascular Research Aug. 15, 1999,vol. 43,No. 3 . . .
International Search Report; PCT/EP2009/052799; dated Aug. 11, 2009.

* cited by examiner

*Primary Examiner* — Chris R Tate
*Assistant Examiner* — Russell Fiebig
(74) *Attorney, Agent, or Firm* — Cantor Colburn LLP

(57) ABSTRACT

L-citrulline for treatment of endothelial dysfunction and in particular of erectile dysfunction and a pharmaceutical composition comprising L-citrulline in combination with one or more substances selected from the group consisting of pycnogenol, aqueous extract of *Viscum album*, NADPH, tetrahydrobiopterin, folic acid and mixtures thereof.

5 Claims, No Drawings ue lyase enzyme into L-arginine and fumarate. The L-arginine thus produced is capable of performing physiological action as a precursor of nitric oxide at the endothelial level.

L-CITRULLINE FOR TREATING ENDOTHELIAL DYSFUNCTION AND ERECTILE DYSFUNCTION

TECHNICAL FIELD

The present invention relates to a compound and a pharmaceutical composition for treating endothelial dysfunction and in particular erectile dysfunction.

BACKGROUND ART

It is now universally acknowledged that endothelial dysfunction, an alteration of the normal biochemical processes normally performed by endothelial tissue which causes several vascular disorders and particularly male erectile dysfunction, is due to the reduced local bioavailability of nitric oxide (NO), the quintessential endogenous vasodilatory substance.

Production of nitric oxide occurs starting from a semi-essential amino acid, L-arginine, which is converted into nitric oxide and citrulline by the nitric oxide synthase (NOS) enzyme. There are three isoforms of this enzyme, designated respectively by the acronyms NOS1 (neuronal), NOS2 (inducible) and NOS3 (endothelial).

Nitric oxide, once produced, enters the smooth muscle cell, where it activates a particular enzyme known as soluble guanylyl cyclase (sGC), with a consequent increase in the quantity of intracellular cyclic guanosine monophosphate (cGMP), reduction in the concentration of $Ca^{2+}$ ion, and consequent vasodilation.

In view of the above, there are three hypothetical ways to act on the decrease in nitric oxide bioavailability: increase the bioavailability of the nitric oxide precursor, i.e., L-arginine; increase the activity of NOS enzymes; and increase the concentration of intracellular cGMP.

The semi-essential amino acid L-arginine is derived mostly from food and only for 5-15% from de novo synthesis. Several metabolic studies have shown that after oral administration, L-arginine is subjected to massive systemic and pre-systemic elimination by intestinal bacteria and by the arginases present in the intestine and liver. A recent experimental study, in which a radioactive isotope of L-arginine was administered, showed that only 1% of the administered dosage is used as a precursor by NOS, mostly due to intense intestinal metabolism. Moreover, it has been demonstrated scientifically that the administration of L-arginine produces blood levels of this amino acid that are characterized by a short half-life, a factor which severely limits the possibility of L-arginine to perform a satisfactory therapeutic effect. Another limitation to oral administration of high doses of L-arginine is the presence of endogenous inhibitors of the reaction for conversion of L-arginine into nitric oxide by NOS. These inhibitors push the activity curve of the enzyme reaction toward higher levels of L-arginine than those administered, an effect acknowledged scientifically as a "paradox effect".

Asymmetric dimethylarginine (ADMA) is an endogenous inhibitor of all three NOS isoforms. ADMA normally circulates in blood at low dosages, but a conspicuous increase thereof is observed in subjects affected by endothelial dysfunction and in particular by erectile dysfunction or in subjects receiving excessive administration of L-arginine. It has been demonstrated scientifically that the ratio between L-arginine and ADMA is one of the key factors in the production of nitric oxide by NOS.

Accordingly, oral administration of L-arginine is unable to increase endogenous production of nitric oxide due to the low absorption of this amino acid caused by: the intense catabolism to which it is subjected in the intestine; its short half-life; and difficulty in modifying the L-arginine/ADMA ratio.

Currently, erectile dysfunction therapy is based substantially on oral administration of phosphodiesterase-5 (PDE5) inhibitors. Drugs containing active ingredients capable of inhibiting PDE5 act by increasing the bioavailability of cGMP at the smooth muscle cell level, inhibiting its catabolism operated by PDE5. However, these drugs are actually unable to increase nitric oxide synthesis and are therefore considered "on demand" drugs, which lead to a temporary increase in erectile functionality.

As an alternative, therapies are being tested for treating erectile dysfunction by direct insertion of the NOS gene at the penile endothelial cell level. This gene therapy procedure uses bacterial vectors to transfer the NOS gene and up to now has proved to be valid in improving erectile function in rats. However, such a method has not yet been developed sufficiently for use in humans; moreover, resorting to gene therapy procedures, and in particular the use of bacterial vectors, is an approach that might be more difficult to accept for a patient with respect to the administration of a drug.

There is, therefore, the need for a drug that can cure endothelial dysfunction and the disorders linked to it by increasing the amount of nitric oxide produced by the body.

DISCLOSURE OF THE INVENTION

The aim of the present invention is to provide a drug that can cure endothelial dysfunction wherever it occurs by means of an increase in the endogenous production of nitric oxide and does not require ad hoc administration to obtain a momentary increase in nitric oxide.

Within this aim, an object of the invention is to provide a drug that is capable of acting in a differentiated but simultaneous manner on the normal biochemical processes that regulate endogenous synthesis of nitric oxide.

Another object of the invention is to provide a drug that leads to an increase in the bioavailability of L-arginine.

Still another object of the present invention is to provide a drug that can induce nitric oxide synthase (NOS) activity.

Finally, an object of the present invention is to provide a drug that can increase the penetration of L-arginine at the endothelial intracellular level.

Other objects, characteristics and advantages of the invention will be described in the foregoing detailed description.

This aim and these and other objects that will become better apparent hereinafter are achieved by L-citrulline for the treatment of endothelial dysfunction or of erectile dysfunction.

The aim and objects of the invention are also achieved by a pharmaceutical composition comprising L-citrulline in combination with one or more substances selected from the group consisting of pycnogenol, aqueous extract of *Viscum album*, nicotinamide adenine dinucleotide phosphate (NADPH), tetrahydrobiopterin, folic acid, and mixtures thereof.

WAYS OF CARRYING OUT THE INVENTION

Without intending to be bound to any theory in particular, it is believed that the therapeutic action of L-citrulline in the treatment of endothelial dysfunction is due to the fact that this non-essential amino acid does not undergo pre-systemic elimination. It is in fact believed that L-citrulline undergoes systemic metabolism, during which it is converted by the L-argininosuccinate synthase enzyme into L-argininosuccinate, which in turn is broken down by the L-argininosuccinase enzyme to yield L-arginine. From this point of view, L-citrulline can be considered as the natural precursor of L-arginine. L-citrulline in fact allows indirectly to increase the bioavailability and plasma half-life of L-arginine, since differently from L-arginine it does not undergo intense intestinal catabolism.

The inventor of the present invention has thus discovered that the administration of L-citrulline, known until now only in the treatment of cardiovascular dysfunctions, is capable of curing endothelial dysfunction wherever it occurs and in particular in the case of erectile dysfunction.

Another embodiment of the present invention consists of the further combination of L-citrulline for the treatment of endothelial dysfunction or of erectile dysfunction with a substance selected from the group consisting of pycnogenol, aqueous extract of *Viscum album*, and mixtures thereof.

Pycnogenol is a plant-derived flavonoid, also known as proanthocyanidin. This substance is contained naturally in many plants, including *Vitis vinifera, Vaccinus myrtillus, Ribes nigrum, Camelia sinensis*, plants of the genus *Aronia* and other plants generally known to contain flavonoids. In particular, it has been observed that pycnogenol is capable of increasing the activity of the NOS3 (endothelial NOS) enzyme at the sperm cell level.

*Viscum album* is a plant known by the more common name of mistletoe. The aqueous extract of this plant has proved to be capable of inducing an overexpression of NOS2 and NOS3 enzymes at the level of muscle cells of the Guinea pigs to which it has been administered.

The inventor of the present invention has discovered that resorting to a combination of L-citrulline with pycnogenol and/or with *Viscum album* extract allows to increase the quantity and activity of endogenous NOS, with a consequent higher production of nitric oxide.

Another embodiment of the present invention also consists of the further combination of L-citrulline for the treatment of endothelial dysfunction or of erectile dysfunction with one or more enzyme cofactors selected from the group consisting of nicotinamide adenine dinucleotide phosphate (NADPH), tetrahydrobiopterin, folic acid and mixtures thereof.

Enzyme cofactors are substances whose presence is required for the optimum biochemical activity of some enzymes. In particular, in the case of the reaction for production of nitric oxide from L-arginine, NOS enzymes use NADPH and tetrahydrobiopterin as essential cofactors.

The inventor of the present invention has discovered that resorting to a combination of L-citrulline with NADPH and/or tetrahydrobiopterin allows to favor the activity of NOS and accordingly the production of nitric oxide.

Moreover, it is known that the rise of blood levels of homocysteine reduces endothelial penetration of L-arginine and that in a patient with endothelial dysfunction, and particularly with erectile dysfunction, blood levels of homocysteine increase. Folic acid, a cofactor of the enzymes involved in the synthesis of homocysteine, has a specific action in lowering the values of homocysteine.

The inventor of the present invention has discovered that resorting to a combination of L-citrulline with folic acid allows to increase endothelial penetration of L-arginine by way of the reduction of homocysteine levels. In turn, this allows a higher inflow of the nitric oxide precursor, L-arginine, at the level of the tissues involved in endothelial and erectile dysfunction.

Therefore, in an embodiment of the present invention, L-citrulline on its own or in combination with one or more substances selected from the group consisting of pycnogenol, aqueous extract of *Viscum album*, NADPH, tetrahydrobiopterin, folic acid, and mixtures thereof can be characterized in that the treatment of the endothelial dysfunction or of the erectile dysfunction occurs by means of the simultaneous increase in the levels of L-arginine and nitric oxide synthase (NOS).

In an embodiment of the present invention, L-citrulline may be administered preferably in a quantity equal to 6 grams/day. For example, daily administration of L-citrulline may be split into two doses of 3 grams each or three doses of 2 grams each.

Moreover, L-citrulline for treating endothelial dysfunction or erectile dysfunction may be used also in combination with other drugs already known for treatment of erectile dysfunction, for example drugs containing PDE5 inhibitors.

In another aspect, the present invention relates also to a pharmaceutical composition characterized in that it comprises L-citrulline in combination with one or more substances selected from the group consisting of pycnogenol, aqueous extract of *Viscum album*, NADPH, tetrahydrobiopterin, folic acid and mixtures thereof.

Of course, the pharmaceutical composition of the present invention may further comprise one or more excipients generally used in pharmaceutical practice.

Moreover, the composition may assume any formulation suitable for its administration to a patient affected by endothelial dysfunction or erectile dysfunction. For example, the composition according to the invention may be in the form of powder, capsules or sachets.

The inventor of the present invention has discovered that the pharmaceutical composition described herein is effective particularly in the treatment of endothelial dysfunction and of erectile dysfunction, and therefore in a preferred embodiment the pharmaceutical composition according to the invention may be used in the treatment of endothelial dysfunction or of erectile dysfunction.

The present invention also relates to a method for treating endothelial dysfunction or erectile dysfunction by administering L-citrulline to a patient, optionally in combination with one or more substances selected from the group consisting of pycnogenol, aqueous extract of *Viscum album*, NADPH, tetrahydrobiopterin, folic acid and mixtures thereof.

Preferably, the method according to the invention may provide for oral administration of L-citrulline.

Moreover, in the method according to the invention L-citrulline may be administered in an amount equal to 6 grams/day. For example, the daily administration of L-citrulline may be split into two doses of 3 grams each or three doses of 2 grams each.

The effectiveness of the administration of L-citrulline in the treatment of erectile dysfunction has been verified by conducting a randomized prospective study on 20 patients, during which L-citrulline was administered orally with a dosage of 6 grams/day, in two separate 3-gram doses, to patients affected by erectile dysfunction. As a comparison, a second group of patients received an administration of L-arginine equal to 3 grams/day, split into two 1.5-gram doses.

The effects of the administration were then tested at the biochemical level by studying the following parameters:
1. plasma levels of L-arginine;
2. blood modification of L-arginine/ADMA ratio;
3. urinary excretion of nitrates;
4. urinary excretion of cGMP.

Moreover, the effects at the clinical level were also tested by administering the "Erectile function assessment card" (IIF-5 questionnaire) to the patients and by measuring flow-mediated vasodilation of the cavernous arteries before and after therapy.

The data related to the above cited biochemical parameters were acquired for patients subjected to the test 7 days after the beginning of the administration of the drug and are shown below in Table 1, Table 2, Table 3 and Table 4.

TABLE 1

Plasma levels of L-arginine (μmol/l)

| Drug | Max plasma concentration |
|---|---|
| L-arginine | 89 ± 10 |
| L-citrulline | 172 ± 25 |

TABLE 2

L-arginine/ADMA ratio

| Drug | baseline | after administration |
|---|---|---|
| L-arginine | 186 ± 7 | 189 ± 10 |
| L-citrulline | 183 ± 8 | 290 ± 15 |

TABLE 3

Urinary excretion of nitrates (nmol/mmol creatinine)

| Drug | baseline | after administration |
|---|---|---|
| L-arginine | 91 ± 10 | 93 ± 12 |
| L-citrulline | 89 ± 9 | 133 ± 16 |

TABLE 4

Urinary excretion of cGMP (nmol/mmol creatinine)

| Drug | baseline | after administration |
|---|---|---|
| L-arginine | 38 ± 3.1 | 39 ± 4.5 |
| L-citrulline | 40 ± 2.8 | 55 ± 3.8 |

The data shown in Tables 1 to 4 allow to observe that oral administration of L-citrulline, with respect to the administration of L-arginine, is able to produce statistically higher plasma levels of arginine and to lead to a statistically longer plasma half-life of L-arginine. Moreover, it should be noted that the administration of L-citrulline also leads to a higher excretion of nitrates and cGMP (measured in terms of nmol/mmol of creatinine), a sign of actual production of nitric oxide by endothelial tissues.

Moreover, from a clinical standpoint, it has been observed that administration of L-citrulline leads to a modification of the IIF-5 questionnaire by patients at the level of the components related to achieving and maintaining erection. Also from a clinical standpoint, a statistically higher increase in flow-mediated vasodilation at the level of the cavernous arteries was also observed with administration of L-citrulline.

In practice it has been found that L-citrulline for treating endothelial dysfunction or erectile dysfunction according to the invention fully achieves the intended aim, since the administration of L-citrulline alone modifies positively and in a statistically significant way the biochemical and clinical parameters linked to erectile dysfunction, thus indicating that the endogenous capacity of tissues to synthesize nitric oxide has been restored.

Moreover, it has been observed that L-citrulline, also thanks to combination with other substances such as pycnogenol, extract of *Viscum album* and enzyme cofactors, allows to act in a differentiated but simultaneous manner on the normal biochemical processes that regulate endogenous synthesis of nitric oxide.

It has in fact been observed that L-citrulline alone or in combination with pycnogenol, extract of *Viscum album* and/or enzyme cofactors allows to increase the bioavailability of L-arginine, induce the activity of NOS enzymes and increase the penetration of L-arginine at the endothelial intracellular level.

The disclosures in Italian Patent Application no. MI2008A000567, from which this application claims priority, are incorporated herein by reference.

The invention claimed is:

1. A method of treating erectile dysfunction comprising administering to a subject in need thereof a composition comprising L-citrulline in combination with an aqueous extract of *Viscum album*, wherein the composition is administered to provide L-citrulline in a dosage of 6 grams/day.

2. The method according to claim 1, wherein the composition further comprises one or more enzyme cofactors selected from the group consisting of NADPH, tetrahydrobiopterin, folic acid and mixtures thereof.

3. The method according to claim 2, wherein the the one or more enzyme cofactors is NADPH.

4. The method according to claim 1, wherein the composition further comprises NADPH.

5. A method of treating erectile dysfunction comprising administering to a subject in need thereof a composition comprising L-citrulline in combination with an aqueous extract of *Viscum album* and pycnogenol, wherein the composition is administered to provide L-citrulline in a dosage of 6 grams/day.

* * * * *